United States Patent
Yamane et al.

(10) Patent No.: US 9,958,399 B2
(45) Date of Patent: May 1, 2018

(54) IMAGING APPARATUS AND IMAGING METHOD

(71) Applicant: KABUSHIKI KAISHA TOSHIBA, Tokyo (JP)

(72) Inventors: Takeshi Yamane, Tsukuba Ibaraki (JP); Tsuneo Terasawa, Tsukuba Ibaraki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 676 days.

(21) Appl. No.: 14/466,181

(22) Filed: Aug. 22, 2014

(65) Prior Publication Data

US 2015/0138344 A1    May 21, 2015

(30) Foreign Application Priority Data

Nov. 15, 2013 (JP) ................... 2013-236685

(51) Int. Cl.
| | |
|---|---|
| *G01N 21/88* | (2006.01) |
| *G02B 19/00* | (2006.01) |
| *G02B 21/08* | (2006.01) |
| *G01N 21/956* | (2006.01) |

(52) U.S. Cl.
CPC ..... *G01N 21/8806* (2013.01); *G02B 19/0023* (2013.01); *G02B 19/0095* (2013.01); *G02B 21/082* (2013.01); *G01N 2021/95676* (2013.01)

(58) Field of Classification Search
None
See application file for complete search history.

(56) References Cited

U.S. PATENT DOCUMENTS

| | | | |
|---|---|---|---|
| 5,085,517 A | 2/1992 | Chadwick et al. | |
| 6,954,266 B2 | 10/2005 | Tomie | |
| 2003/0067598 A1 | 4/2003 | Tomie | |
| 2006/0290923 A1 | 12/2006 | Nakano et al. | |
| 2007/0223112 A1* | 9/2007 | Mann ............... | B82Y 10/00 359/726 |
| 2010/0165310 A1* | 7/2010 | Sewell ............. | G03B 27/42 355/53 |

(Continued)

FOREIGN PATENT DOCUMENTS

| | | | | |
|---|---|---|---|---|
| JP | 63118275 A | * | 5/1988 | ............ G06K 1/126 |
| JP | 10-093764 | | 4/1998 | |

(Continued)

*Primary Examiner* — Janese Duley
(74) *Attorney, Agent, or Firm* — Finnegan, Henderson, Farabow, Garrett & Dunner, L.L.P.

(57) ABSTRACT

According to one embodiment, an imaging apparatus includes a light source for illumination, a stage on which an imaging object illuminated by illumination light from the light source is to be placed, a critical illumination optical system configured to supply the illumination light to the imaging object placed on the stage, and to have a greater magnification in a first axis direction than in a second axis direction, an imaging optical system configured to form an image of the imaging object placed on the stage and illuminated using the critical illumination optical system, and a detector configured to detect the image of the imaging object formed by the imaging optical system, and to have a detection area longer in the first axis direction than in the second axis direction.

10 Claims, 3 Drawing Sheets

(56) References Cited

U.S. PATENT DOCUMENTS

2010/0238442 A1  9/2010 Heng et al.

FOREIGN PATENT DOCUMENTS

| | | |
|---|---|---|
| JP | 2002-174514 | 6/2002 |
| JP | 2002-318157 | 10/2002 |
| JP | 2002-340815 | 11/2002 |
| JP | 2007-33433 | 2/2007 |

* cited by examiner

IMAGING APPARATUS AND IMAGING METHOD

CROSS-REFERENCE TO RELATED APPLICATIONS

This application is based upon and claims the benefit of priority from Japanese Patent Application No. 2013-236685, filed Nov. 15, 2013, the entire contents of which are incorporated herein by reference.

FIELD

Embodiments described herein relate generally to an imaging apparatus and an imaging method.

BACKGROUND

As semiconductor devices are miniaturized, mask inspection is hard to be performed with high accuracy in a short time. In particular, the mask inspection of a reflective mask using an extreme ultraviolet (EUV) illumination light is very hard to be performed with high accuracy in a short time.

A time delay integration (TDI) method using a two-dimensional detector is effective as a method for performing the mask inspection in a short time. However, the two-dimensional detector is hard to be higher in density since an interconnect area has to be secured.

On the other hand, a one-dimensional detector can achieve high density, but the TDI method cannot be used. Thus, an exposure time needs to be increased to secure fixed exposure amount or more, and high-accuracy inspection is hard to be performed in a short time.

As described above, conventionally, it was difficult to obtain an imaging apparatus which can detect a defect image with high accuracy in a short time. Therefore, an imaging apparatus and an imaging method enabling imaging with high accuracy in a short time are desired.

DETAILED DESCRIPTION

In general, according to one embodiment, an imaging apparatus includes: a light source for illumination; a stage on which an imaging object illuminated by illumination light from the light source is to be placed; a critical illumination optical system configured to supply the illumination light from the light source to the imaging object placed on the stage, and to have a greater magnification in a first axis direction than in a second axis direction perpendicular to the first axis direction; an imaging optical system configured to form an image of the imaging object placed on the stage and illuminated using the critical illumination optical system; and a detector configured to detect the image of the imaging object formed by the imaging optical system, and to have a detection area longer in the first axis direction than in the second axis direction.

Various embodiments will be described hereinafter with reference to the accompanying drawings.

First Embodiment

Figure 1:
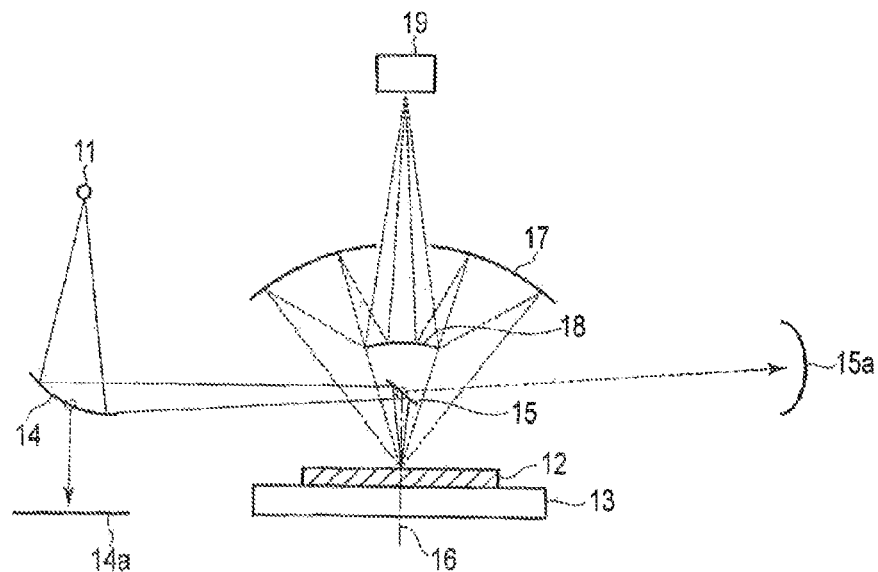
FIG. 1 is a schematic view showing a structure of an imaging apparatus according to a first embodiment.

FIG. 1 is a schematic view showing a structure of an imaging apparatus according to a first embodiment. An imaging apparatus according to this embodiment is used for defect inspection of an exposure mask which is used in a lithography process of a semiconductor device (semiconductor integrated circuit device). Specifically, the imaging apparatus of this embodiment is applied to defect inspection of a reflective mask used in a lithography process in which extreme ultraviolet (EUV) illumination light is used.

EUV illumination light for inspection is given off from a light source 11 for illumination. An exposure mask (imaging object) 12 illuminated by illumination light from the light source 11 is placed on a stage 13.

The illumination light from the light source 11 is supplied to a surface of the exposure mask 12 placed on the stage 13 through a critical illumination optical system. In the critical illumination optical system, a magnification in an X-axis (first axis) direction is larger than that in a Y-axis (second axis) direction perpendicular to the X-axis direction, where the X-axis is parallel to the paper surface, the Y-axis is perpendicular to the paper surface, and Z-axis is the optical axis. It should be noted that the critical illumination optical system is an illumination optical system in which an image of a light source is formed on a surface of an object to be measured (here, exposure mask). That is, the critical illumination optical system is an illumination optical system in which the image of the light source is formed on the surface of the object to be measured (exposure mask) both in the X- and Y-axis directions.

The critical illumination optical system comprises a cylindrical mirror 14 and a cylindrical mirror 15. The illumination light from the light source 11 is reflected by the cylindrical mirrors 14 and 15, and irradiated on the exposure mask 12 arranged perpendicular to a light axis 16.

Figure 2:
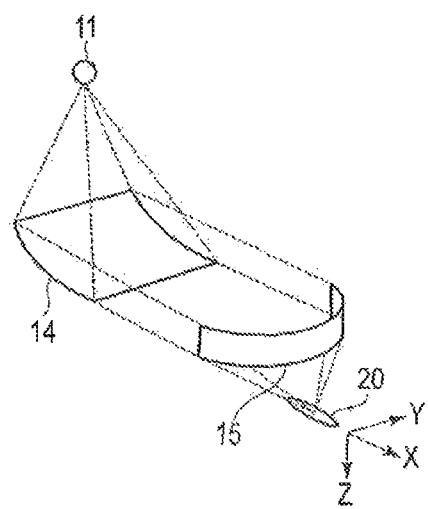
FIG. 2 is a schematic view showing a positional relationship of two cylindrical mirrors in the first embodiment.

FIG. 2 is a schematic view showing a positional relationship between the cylindrical mirrors 14 and 15. As shown in FIGS. 1 and 2, a section of the cylindrical mirror 14 that is parallel to the X-axis of the cylindrical mirror 14 is a curved line constituting a part of an ellipse. Also, a section of the cylindrical mirror 14 that is parallel to the Y-axis of the cylindrical mirror 14 is a straight line. In FIG. 1, the section of the cylindrical mirror 14 that is parallel to the Y-axis of the cylindrical mirror 14 is represented as section 14a. A section of the cylindrical mirror 15 that is parallel to the X-axis of the cylindrical mirror 15 is a straight line. Also, a section of the cylindrical mirror 15 that is parallel to the Y-axis of the cylindrical mirror 15 is a curved line constituting a part of an ellipse. In FIG. 1, the section of the cylindrical mirror 15 that is parallel to the Y-axis of the cylindrical mirror 15 is represented as section 15a.

Curvatures and positions of the cylindrical mirrors 14 and 15 are determined to form the image of the light source on the surface of the exposure mask 12. That is, the curvatures and positions of the cylindrical mirrors 14 and 15 are determined to form critical illumination.

As described above, the light source 11, an elliptical arc shape mirror 14 and a linear mirror 15 are arranged in this order along the X-axis. The light source 11, a linear mirror 15 (15a) and an elliptical arc shape mirror 14 (14a) are arranged in this order along the Y-axis. That is, the elliptical arc shape mirror is arranged closer to the light source 11 on the X-axis than on the Y-axis. Thus, the magnification on the X-axis is greater than that on the Y-axis. If the shape of the light source is a circle as shown in FIG. 2, an elliptical illumination area 20 having a long X-axis and a short Y-axis is formed on the surface of the exposure mask 12.

The illumination light from the light source 11 is supplied to the exposure mask 12 placed on the stage 13, and the illumination area 20 is formed on the surface of the exposure mask 12 in the above manner, using the critical illumination optical system (cylindrical mirrors 14 and 15) in which the magnification on the X-axis is greater than that on the Y-axis.

An image of the exposure mask 12 placed on the stage 13 is formed by an imaging optical system. The imaging optical system comprises a concave mirror 17 and a convex mirror 18. The image of the exposure mask 12 is reflected by the concave mirror 17 and the convex mirror 18.

The image of the exposure mask 12 formed by the imaging optical system (concave mirror 17 and convex mirror 18) is detected by a one-dimensional detector 19. In the one-dimensional detector 19, the detection area is longer in the X-axis (first axis) direction than in the Y-axis (second axis) direction. Specifically, the one-dimensional detector 19 includes a plurality of pixels one-dimensionally arrayed along the X-axis. For example, a CCD in which pixels are one-dimensionally arrayed can be used for the one-dimensional detector 19.

Figure 3:
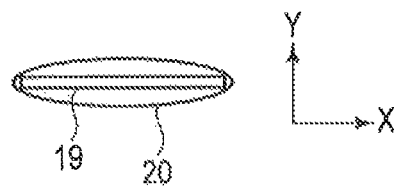
FIG. 3 shows a relationship between a detector and an illumination area in the first embodiment.

FIG. 3 shows a relationship between the one-dimensional detector 19 and the illumination area 20. As shown in FIG. 3, the long axes (long sides) of both the one-dimensional detector 19 and illumination area 20 are the X-axis. That is, the long axis (long side) of the one-dimensional detector 19 matches the long axis of the illumination area 20. Also, the ratio of the magnification on the X-axis to that on the Y-axis in the critical illumination optical system is equal to the ratio of the length of the detection area along the X-axis (long axis, long side) to that along the Y-axis (short axis, short side).

When the image of the exposure mask 12 is detected by the one-dimensional detector 19, the stage 13 and the detector 19 are relatively scanned along the Y-axis. Specifically, while the stage 13 on which the exposure mask 12 is placed is scanned along the Y-axis, image intensity is obtained by the one-dimensional detector 19. The image intensity in the positional coordinates (x, y) is obtained, where (x, y) are the positional coordinates on the surface of the exposure mask 12 of the image detected by each pixel of the one-dimensional detector 19. By plotting the image intensity as a function of the positional coordinates (x, y), a dark-field image of the exposure mask 12 can be obtained. The dark-field image of the whole of the exposure mask 12 can be obtained by scanning the whole of the exposure mask 12.

Figure 4:
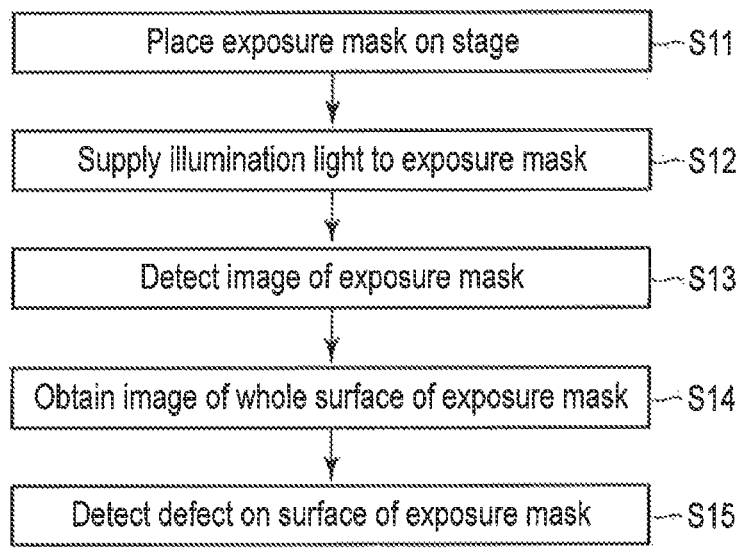
FIG. 4 is a flowchart showing an imaging method and a defect inspection method according to the first embodiment.

FIG. 4 is a flowchart showing an imaging method and a defect inspection method in which the imaging apparatus is used.

First, the imaging apparatus shown in FIG. 1 is prepared, and the exposure mask 12 is placed on the stage 13 (S11).

Next, the illumination light is supplied from the light source 11 to the exposure mask 12 placed on the stage 13, using the critical illumination optical system (cylindrical mirrors 14 and 15) (S12). An elliptical illumination area having a long X-axis and a short Y-axis is formed on the surface of the exposure mask 12.

Next, the image of the exposure mask 12 formed by the imaging optical system (concave mirror 17 and convex mirror 18) is detected by the one-dimensional detector 19 (S13). The long axis (long side) and short axis (short side) of the detection area of the one-dimensional detector 19 correspond to the long axis and short axis of the illumination area, respectively.

Steps S12 and S13 are repeatedly carried out by shifting the stage 13 along the Y-axis, and then the image of the whole surface of the exposure mask 12 (dark-field image) is obtained (S14).

The defect on the surface of the exposure mask 12 is detected based on the image of the exposure mask 12 obtained as described above (S15).

In this manner, photolithography is performed using the exposure mask 12 which is imaged and on which defect inspection is performed, and a semiconductor device is manufactured.

In this embodiment, as described above, the image of the exposure mask (object to be measured) is detected by the detector having a detection area longer along the X-axis than along the Y-axis, using the critical illumination optical system having a greater magnification on the X-axis (first axis) than that on the Y-axis (second axis) perpendicular to the X-axis. Thus, the long axis of the illumination area corresponds to the long axis (long side) of the detector, and the illumination light from the light source can be efficiently supplied to the illumination area necessary for the inspection. That is, the illumination light from the light source can be efficiently supplied to the illumination area corresponding to the detection area of the detector. Consequently, the ratio of an illumination area unnecessary for inspection can be made small, and even if illumination time (exposure time) is shortened, fixed illumination intensity (exposure intensity) or more can be secured. Thus, in this embodiment, high-accuracy imaging can be performed in a short time, and high-accuracy inspection can be efficiently performed.

Also, since the illumination light can be efficiently supplied to the illumination area, the detector can be made longer along the long axis. Accordingly, a broad area can be imaged by carrying out scanning once, and high-accuracy inspection can be performed in a short time.

Also, in this embodiment, the ratio of the magnification on the X-axis of the illumination optical system to that on the Y-axis is equal to the ratio of the length of the long axis (long side) (length on the X-axis) of the one-dimensional detector to that of the short axis (short side) (length on the Y-axis). Thus, the illumination light can be more efficiently supplied, and the above-described effect can be more suitably obtained.

Also, high-accuracy imaging can be performed using the one-dimensional detector enabling density growth, and the above-described advantage can be more suitably obtained.

It should be noted that although a one-dimensional detector is used for a detector in the above embodiment, a two-dimensional detector including a plurality of pixels two-dimensionally arrayed can also be used. Also in this case, the illumination light from the light source can be efficiently supplied to the illumination area necessary for the inspection by associating the long axis of the illumination area with the long axis (long side) of the two-dimensional detector, and an advantage similar to the above advantage can be obtained.

If a two-dimensional detector is used, the ratio of the magnification on the X-axis of the illumination optical system to that on the Y-axis should be equal to the ratio of the length of the long axis (long side) (length on the X-axis)

of the two-dimensional detector to that of the short axis (short side) (length on the Y-axis) in the same manner as in the above embodiment. By such a structure, the illumination light can be more efficiently supplied, and the above advantage can be more suitably obtained.

Also, although image intensity may be output for each pixel in the above embodiment, the total sum of the image intensity obtained by each pixel in a pixel block comprising a plurality of pixels may be output for each pixel block. Accordingly, the detection variation can be reduced by the pixel block comprising the plurality of pixels.

Second Embodiment

Figure 5:
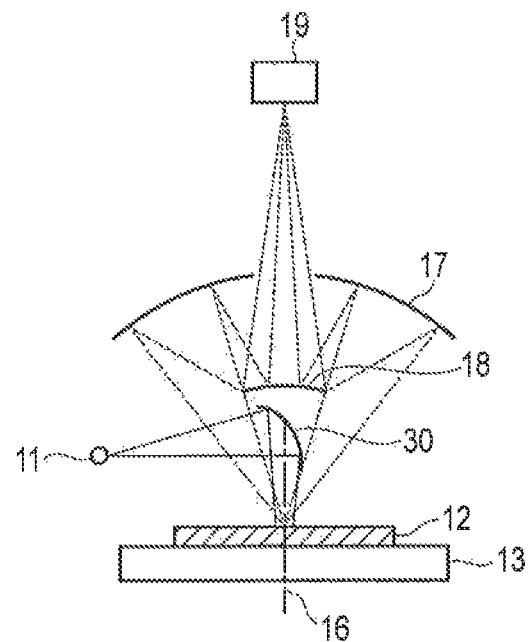
FIG. 5 is a schematic view showing a structure of an imaging apparatus according to a second embodiment.

FIG. 5 is a schematic view showing a structure of an imaging apparatus according to a second embodiment. It should be noted that since basic matters are similar to those in the first embodiment, description of the matters described in the first embodiment will be omitted.

An imaging apparatus of this embodiment, as well as that of the first embodiment, is used for inspection of an exposure mask used in a lithography process of a semiconductor device (semiconductor integrated circuit device). Specifically, the imaging apparatus of this embodiment is applied to inspection of a reflective mask used in the lithography process in which an EUV illumination light is used.

Basic matters concerning the light source 11, the exposure mask (imaging object) 12, the stage 13, the imaging optical system (concave mirror 17 and convex mirror 18) and the one-dimensional detector 19 are similar to those in the first embodiment.

In this embodiment, a toroidal mirror 30 is used as an illumination optical system, although the cylindrical mirrors 14 and 15 are used in the first embodiment.

The illumination light from the light source 11 is reflected by the toroidal mirror 30, and supplied to the surface of the exposure mask 12 placed on the stage 13. The toroidal mirror 30 is a mirror having different curvatures between the X-axis (first axis) (parallel to the paper surface) and the Y-axis (second axis) (perpendicular to the paper surface) perpendicular to the X-axis. In this embodiment, when the illumination light from the light source 11 is supplied to the exposure mask 12 placed on the stage 13 through the toroidal mirror 30, the curvatures and position of the toroidal mirror 30 are determined in order not to form an image of a light source on the surface of the exposure mask 12 on the X-axis, and in order to form the image of the light source on the surface of the exposure mask 12 on the Y-axis.

By using the toroidal mirror, astigmatism occurs in the image of the light source, and an elliptical illumination area having a long X-axis and a short Y-axis is formed on the surface of the exposure mask 12.

The image of the surface of the exposure mask 12 placed on the stage 13 and illuminated using the illumination optical system (toroidal mirror 30) is formed by the imaging optical system (concave mirror 17 and convex mirror 18).

The image of the exposure mask 12 formed by the imaging optical system (concave mirror 17 and convex mirror 18) is detected by the one-dimensional detector 19. In the one-dimensional detector 19, the detection area is longer along the X-axis (first axis) than along the Y-axis (second axis). A specific structure of the one-dimensional detector 19 is similar to that in the first embodiment.

The one-dimensional detector 19 and the illumination area 20 have a relationship as shown in FIG. 3 in the same manner as in the first embodiment. That is, the long axis (long side) of the one-dimensional detector 19 matches the long axis of the illumination area 20.

When the image of the exposure mask 12 is detected by the one-dimensional detector 19, the stage 13 on which the exposure mask 12 is placed is scanned along the Y-axis, and image intensity is obtained by the one-dimensional detector 19, as in the first embodiment. Consequently, a dark-field image of the whole exposure mask 12 can be obtained as well as in the first embodiment.

As described above, the relationship between the illumination area formed by the illumination optical system (toroidal mirror) and one-dimensional detector in this embodiment is similar to that in the first embodiment. Thus, an advantage similar to that in the first embodiment can also be obtained in this embodiment.

It should be noted that since basic imaging and defect detection methods using the imaging apparatus are similar to those in the first embodiment, their description will be omitted.

Also, various changes similar to those described in the first embodiment can also be made in this embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging apparatus comprising:
a light source for illumination;
a stage on which an imaging object illuminated by illumination light from the light source is to be placed;
a critical illumination optical system configured to supply the illumination light from the light source to the imaging object placed on the stage, and to have a greater magnification in a first axis direction than in a second axis direction perpendicular to the first axis direction;
an imaging optical system configured to form an image of the imaging object placed on the stage and illuminated using the critical illumination optical system;
an elliptical arc shape mirror and a linear mirror, the elliptical arc shape mirror being arranged closer to the light source along the first axis direction than the second axis direction; and
a detector configured to detect the image of the imaging object formed by the imaging optical system, the detector having a detection area longer in the first axis direction than in the second axis direction, and including a plurality of pixels arrayed in the first axis direction.

2. The apparatus of claim 1, wherein a ratio of the magnification in the first axis direction to the magnification in the second axis direction in the critical illumination optical system corresponds to a ratio of a length of the detection area in the first axis direction to a length of the detection area in the second axis direction.

3. The apparatus of claim 1, wherein the detector includes a plurality of one-dimensionally arrayed pixels.

4. The apparatus of claim 1, wherein the imaging object is an exposure mask.

5. The apparatus of claim 1, wherein the elliptical arc shape mirror and the linear mirror are cylindrical mirrors.

6. An imaging method comprising:
supplying illumination light from a light source to an imaging object placed on a stage using a critical illumination optical system configured to have a greater magnification in a first axis direction than in a second axis direction perpendicular to the first axis direction, the optical system having an elliptical arc shape mirror and a linear mirror, the elliptical arc shape mirror being arranged closer to the light source along the first axis direction than the second axis direction; and
detecting an image of the imaging object formed by an imaging optical system by a detector, the detector having a detection area longer in the first axis direction than in the second axis direction and including a plurality of pixels arrayed in the first axis direction.

7. The method of claim 6, wherein a ratio of the magnification in the first axis direction to the magnification in the second axis direction in the critical illumination optical system corresponds to a ratio of a length of the detection area in the first axis direction to a length of the detection area in the second axis direction.

8. The method of claim 6, wherein the detector includes a plurality of one-dimensionally arrayed pixels.

9. The method of claim 6, wherein the imaging object is an exposure mask.

10. The method of claim 6, wherein the elliptical arc shape mirror and the linear mirror are cylindrical mirrors.

* * * * *